(12) United States Patent
Chen et al.

(10) Patent No.: US 8,610,885 B2
(45) Date of Patent: Dec. 17, 2013

(54) COATED OPTICAL-FIBER BEND-FATIGUE AND RELIABILITY TESTER

(75) Inventors: David Zhi Chen, Richardson, TX (US); Vijay Jain, Friendship, MD (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 419 days.

(21) Appl. No.: 12/817,811

(22) Filed: Jun. 17, 2010

(65) Prior Publication Data

US 2011/0313683 A1 Dec. 22, 2011

(51) Int. Cl.
*G01N 21/00* (2006.01)
(52) U.S. Cl.
USPC ............................................. 356/73.1
(58) Field of Classification Search
USPC ....................................... 356/73.1
See application file for complete search history.

(56) References Cited

U.S. PATENT DOCUMENTS

| 4,996,420 A | * | 2/1991 | Redford | 250/227.24 |
| 2006/0045408 A1 | * | 3/2006 | Jones et al. | 385/12 |

* cited by examiner

*Primary Examiner* — Tara S Pajoohi Gomez

(57) ABSTRACT

Apparatus and methodology for testing coated optical-fiber bend fatigue and operational reliability by subjecting a coated optical-fiber carrying an optical signal to bending motion. The motion can be either: (1) in the same angular direction for multiple revolutions or (2) alternating clockwise and counterclockwise directions for repetitive single revolutions. The motions are achieved by using either a single conical-cylindrical form or two conically-shaped forms separated from each other by a constant gap width with the coated optical-fiber under test strung in the gap between the forms. With the two cones, the fiber is wrapped over each form in an alternating manner by a rotating arm that makes only single revolutions in clockwise and counterclockwise directions. With either embodiment, varied circumferences are controllably presented to the optical fiber resulting in varying bend radii. Fiber tension, signal strength and optical wavelength are parameters that can also be varied under computer control, the computer providing spreadsheet data for clear analysis.

42 Claims, 9 Drawing Sheets

| OPTICAL FIBER SAMPLE # | OPTICAL SIGNAL WAVELENGTH | OPTICAL SIGNAL POWER | BEND RADIUS (FIXED) | BEND RADIUS (VARYING) | FIBER TENSION | RETURN SIGNAL % DETERIORATION AFTER #/OF BENDS | FIBER FRACTURE AFTER #/OF BENDS |
|---|---|---|---|---|---|---|---|
| A | | | | | | | |
| B | | | | | | | |
| C | | | | | | | |

FIG. 7

COATED OPTICAL-FIBER BEND-FATIGUE AND RELIABILITY TESTER

BACKGROUND

Fiber optic cable contains multiple, mutually-isolated, coated optical-fibers. The cable is flexible and, during installation, e.g., in an existing dwelling or multi-dwelling unit, aggressive bending may be required to avoid obstruction. Accordingly, each individual coated optical-fiber in the cable is subjected to the same bending.

Each mutually-isolated optical-fiber has glass at its core and cladding to form a proper boundary condition for the wave guide. The clad glass is coated with a soft coating/cushion which, in turn, is covered by a hard coating protection layer. Finally, a plurality of those optical-fibers is cabled to a needed diameter to form a useful cable.

When a fiber optic cable is bent, mechanical stresses are developed in the glass of its encapsulated fibers, in their coatings and finally in the cable, i.e., compression in the glass and coatings of a glass fiber at the inside of the bend and tensile force in that glass and coatings at the outside of the bend. The soft coating/cushion helps to reduce the stresses on the glass of the coated optical-fiber when it is bent and the hard coating prevents the coating from breaking away from the fiber cladding while also protecting the glass core/cladding and soft coating. Traditionally, fiber could not be bent below 15 mm bend radius (established by industry standard G.652-D), because below a 15 mm bend radius, light would leak out of the fiber cladding, and the result could be a very high light energy loss.

However, the new Bend Insensitive Fiber (industry standard G.657-B3) has a bend radius limit targeted at a much lower 5 mm radius. At this bend radius, fiber is under extreme stress, much greater stress than at 15 mm, and the fiber may break before observing a major insertion loss. At these small radii, the coating on the cladding may tend to fail in its protection role at locations of severe bends in the cable (i.e., bends having small bend-radii such as under 5 millimeters, per industry standard G.657-B-3). It appears that optical performance may now be surpassing coating performance in an optical fiber. In order to protect the fiber under this tight bend, some new coating technologies have been, and are being, developed. Exemplary embodiments relate to novel apparatus and methodology for determining robustness of various new coatings by subjecting those coatings to a proper fiber bend stress tolerance test technique.

A newer optical cable with improved coatings can protect the fiber from breaking, even for much smaller radii such as 5 millimeters although, as noted, tremendous compression and tensile forces are imposed on the newer glass core/cladding at such minimal bend radii. (The bigger the radius the lower the tension/compression forces, and the smaller the radius the higher the forces.) Therefore, there no longer is a radiation-leakage early warning of impending failure provided by the newer cable. Sudden, catastrophic failure, due to optical-fiber glass fracture, or the like, can be experienced by optical communication system users without any warning, to their dismay.

Therefore, there is a need to design better coated optical-fiber cables with improved coating systems to reduce the likelihood of glass fracture at locations of severe bends. The novel technique disclosed herein for testing bend fatigue and determining reliability of coated optical-fibers supports efforts for achieving new and improved coated optical-fiber designs.

BRIEF DESCRIPTION OF THE DRAWINGS

FIG. 7 is an exemplary table or spreadsheet showing multiple variables that can be input and controlled in the testing of coated optical-fibers;

DETAILED DESCRIPTION OF PREFERRED EMBODIMENTS

Figure 1:
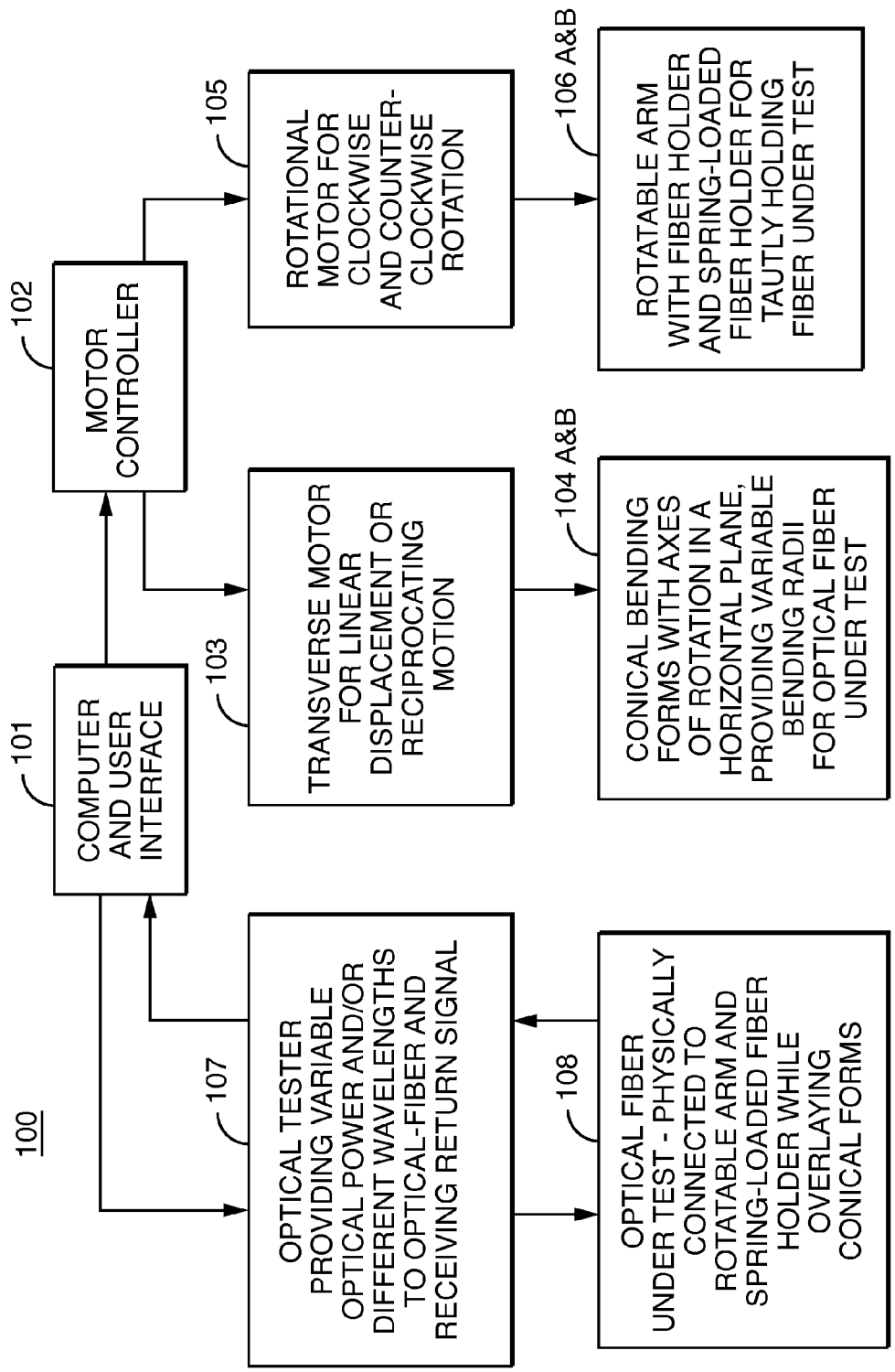
FIG. 1 is an exemplary system block diagram of functions performed by exemplary embodiments.

In this description, the same reference numeral in different Figs. refers to the same entity. Otherwise, reference numerals of each FIG. start with the same number as the number of that FIG. For example, FIG. 3 has numerals in the "300" category and FIG. 4 has numerals in the "400" category, etc.

In overview, preferred embodiments include apparatus and methodology for testing performance of a coated optical-fiber by monitoring an optical signal being continuously transmitted through that fiber while simultaneously subjecting that fiber to mechanical stress from repetitive bending and straightening. In a particular embodiment the bending is limited to a bend-radius no less than a radius value included within a controllable bend-radius range of minimal values. Further, an optical tester is provided which is operatively connected to both ends of the coated optical-fiber under test. An optical signal is transmitted via one of the ends of the coated optical-fiber and is received from the other end, while the repetitive bending and straightening is occurring. The received optical signal is compared with the transmitted optical signal to provide information about the condition of the coated optical-fiber.

In a further feature, apparatus and methodology are provided for bending the fiber in a clockwise direction and, after straightening the fiber, bending the fiber in a counterclockwise direction and repeating this process. In a particular configuration, two conically-shaped forms having their axes of rotation lying in a horizontal plane taper in a common direction towards the location of an axel powered by a rotational motor. The two conical forms have their respective surfaces separated from each other by a fixed gap distance being slightly larger than a diameter of a coated optical-fiber to be tested. The coated optical-fiber is strung in the gap between the two conical forms, and is attached to an end of a rigid arm fixedly-extended from the axel which is powered by the rotational motor. The axel has an axis of rotation parallel to the direction of the gap, where that axis of rotation and a longitudinal midpoint line in the gap may both lie in the same vertical plane.

The axel and its fixedly-attached arm rotate together in alternate clockwise and counter-clockwise half-circles, if measured from a neutral-vertical position (i.e. 12:00 o'clock). The coated optical-fiber in the gap between the two conical forms is first overlayed on the surface of one conical form and then, when the arm moves to the limit in the opposite angular direction, the fiber is overlayed on the surface of the other conical form. This clockwise and counter-clockwise motion causes approximate semi-circular bending in both clockwise and counter-clockwise directions and is repeated until the test of the coated optical-fiber is completed.

The locus of points on the surface of each conical form representing contact with the coated optical-fiber is not truly semi-circular, but is a portion of an ellipse. It is not a semi-circle because the axes of rotation of the cones are not parallel to each other and not parallel to the axis of rotation of the axel; rather, the axis of rotation of the axel is essentially parallel to the longitudinal direction of the fixed gap separating the two conical forms at their closest location to each other. To accommodate the constant gap width between cones, the axes of rotation of the cones point in directions which, if sufficiently extended, would intersect. The overlayment of the coated optical-fiber by the rotational motion is not perpendicular to the axes of rotation of the cones wherefore an elliptical, rather than circular, contact is made between the coated optical-fiber and the conical-form surfaces. Thus, even when the conical forms are fixed in location and not moving in a direction parallel to the direction of the gap, described below, the bend-radius associated with the coated optical-fiber varies slightly as a function of the instantaneous radius of curvature of the elliptical locus of points.

In addition, the conical members can be controlled to move in a direction parallel to the gap. The gap is also parallel to the axis of the rotatable axel. The two conical forms are fixedly mounted to a transverse-movement, or reciprocating, motor which, when operating, moves both conical forms together in a horizontal direction parallel to the gap and to the axis of the axel. The bend radius changes between upper and lower radius limits as a function of location of the conical forms relative to the location of the optical fiber which, in turn, is pegged to the location of the rotatable axel. Thus, for movement towards the location of the rotatable axel, because the conical forms "point" in the direction of the axel, the bend-radius associated with the coated optical-fiber increases, putting less stress on the glass fiber. For movement away from the location of the rotatable axel, the bend radius associated with the coated optical-fiber decreases, putting more stress on the glass fiber.

FIG. 1 is an exemplary system block diagram 100 of functions performed by an exemplary embodiment. Computer and user interface 101 is conventional and available in the marketplace. It provides commands to motor controller 102 which controls both transverse, reciprocating motor 103 and rotational motor 105. Control signals provided by motor controller 102 can change a fixed position of conical bending forms 104 along a line in the direction of the gap between the forms to a different fixed position. However, if not in fixed position operating mode, but in the continually-varying transverse movement mode, motor controller 102 can increase or decrease frequency of motion of reciprocating motor 103. Motor Controller 102 can also increase or decrease the frequency of rotational motion of rotational motor 105 which controls motion of the rotatable arm portion of functionality included in functional block 106. Motor controller 102 can make both frequencies identical or can make the frequency of either motor greater than the other by integer multiples or by fractions of integer multiples.

Computer and user interface 101 also permits a user, by way of a graphical user interface (GUI) or by other computer input, to control optical tester 107 which may be an optical time domain refractometer (OTDR) or an instrument related to an OTDR which can compare two optical signals in a manner desired by those conducting the test of the coated optical-fiber under test 108. Optical tester 107 can change parameters or variables associated with the test such as optical signal power and optical signal wavelength. These variables can be changed in synchrony with changes to bend-radius in any manner. In other words, optical power can increase or decrease while bend-radius can increase or decrease. Further, these conditions can be imposed on the tester at each of several different optical signal wavelengths such as, for example 1310 nanometers (nm), 1490 nm, 1550 nm, and 1625 nm. Further, these conditions can be imposed on the tester while the tension imposed on coated optical-fiber under test 108 is controlled at a particular tension value.

Figure 2:
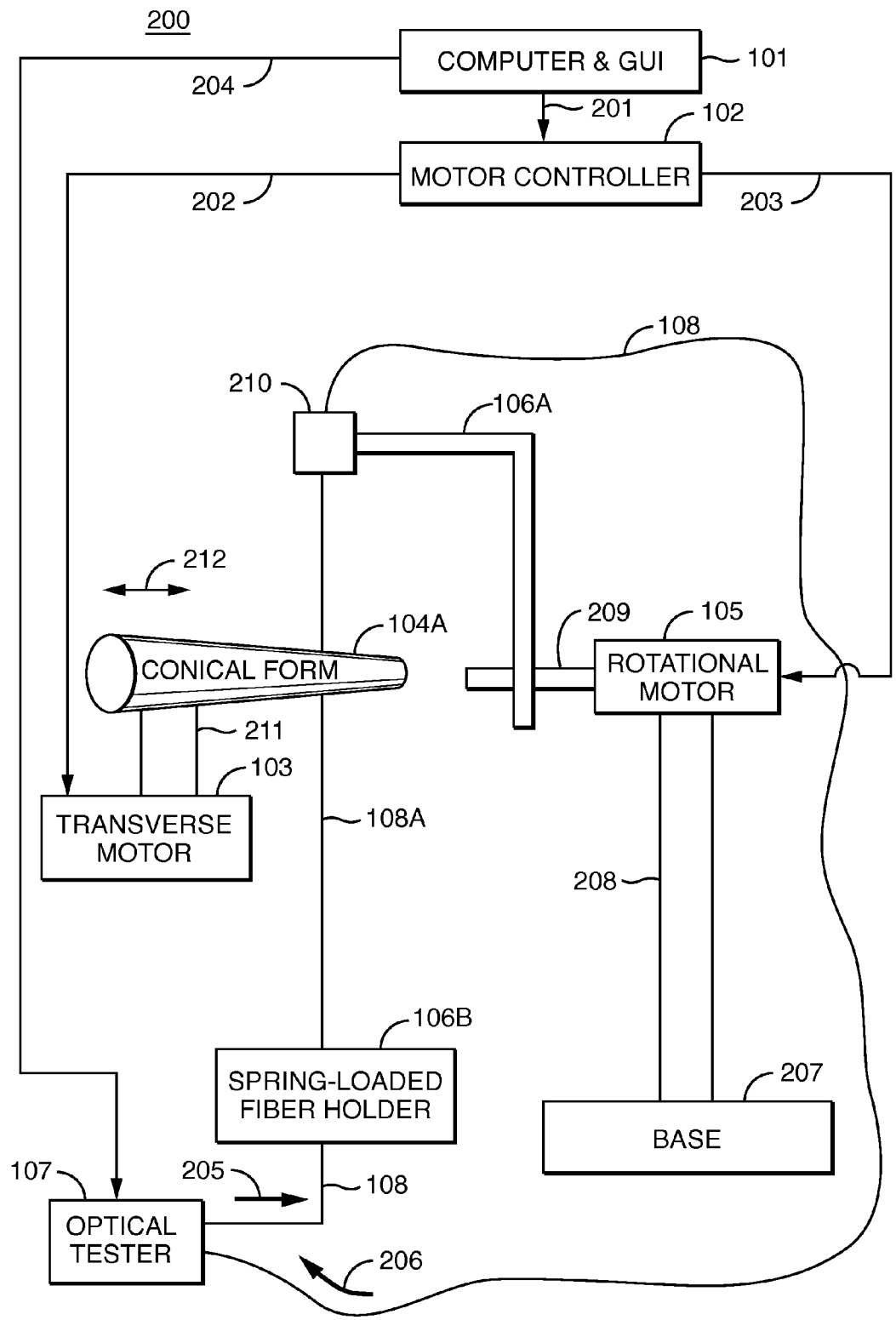
FIG. 2 is an exemplary schematic diagram of apparatus employed in exemplary embodiments to provide the functionality depicted in FIG. 1.

FIG. 2 is an exemplary schematic diagram of apparatus 200 employed by exemplary embodiments to provide functionality depicted in FIG. 1. Computer and GUI 101 (graphical user interface) provide overall control of the testing operation and processing of test results. The GUI is provided for a user to interface with the computer which has been programmed to supervise the motor controller 102 via control line 201 and to supervise optical tester 107 via control line 204. The computer is conventional, can be of any available configuration such as laptop, desktop, etc. The computer can be part of a network in a client-server or other architecture. The network can be any network such as, for example, a local area network (LAN), wide area network (WAN), or a packet-switched network such as the Internet, where optical-fiber test results can be shared with other interested parties.

Controller 102 controls transverse motor 103 via control line 202 to provide linear displacement of conical forms 104A/B (only A showing in this FIG.) in directions 212 by moving conical-form support 211 which is attached to the conical forms. Controller 102 also controls rotational motor 105 via control line 203 to provide alternate clockwise and counter-clockwise single revolutions of axel 209 which is operatively connected to rigid support arm 106A which, in turn, supports optical-fiber holder 210. Holder 210 is shown in the FIG. at a midpoint location within a single revolution with coated optical-fiber 108 attached. Coated optical-fiber 108 is constrained to first overlay or wrap-over conical form 104A and, thereafter, conical form 104B (104B not shown in FIG. 2). Thus, coated optical-fiber 108 bends in either angular direction, alternately, as a result of the rotational motion being described.

Rotational motor 105 is held firm by upright legs 208 (one showing in FIG. 2) which, in turn, are supported by fixed base 207. Rotational axel 209 is connected from motor 105 and is rigidly connected to support arm 106A which, in turn, is rigidly attached to fiber holder 210. Holder 210 rotates clockwise and counter-clockwise (in a plane perpendicular to the plane of the drawing) to a limit stop which allows it to rotate from the neutral position shown directly above a gap (gap shown in FIG. 3) between conical form 104A and conical form 104B (104B shown in FIG. 3) to directly below the gap. In other words, if measured from its position directly below the gap, holder 210 makes only one revolution in either a clockwise direction or a counter-clockwise direction, always stopping at its limit stop directly below the gap, and then repeating with the opposite motion from the last motion performed.

Spring-loaded fiber holder 106B is configured to control tension within that portion of coated optical-fiber 108, designated 108A, held directly between spring-loaded fiber holder 106B and optical-fiber holder 210, both of which are conventional equipment. Coated optical-fiber 108A is held tautly and at a near constant tension value. In an alternative embodiment, spring-loaded fiber holder 106B can also be controlled by computer and GUI 101 to allow optical-fiber portion 108A to have other tension values. An optical signal is transmitted from optical tester 107 on fiber 108 in direction 205 and is returned to optical tester 107 on coated optical-fiber 108 in direction 206, and this transmission takes place concurrently with the described rotational motions. Optical tester can be a conventional optical tester, such as an OTDR, available in the marketplace.

Figure 3:
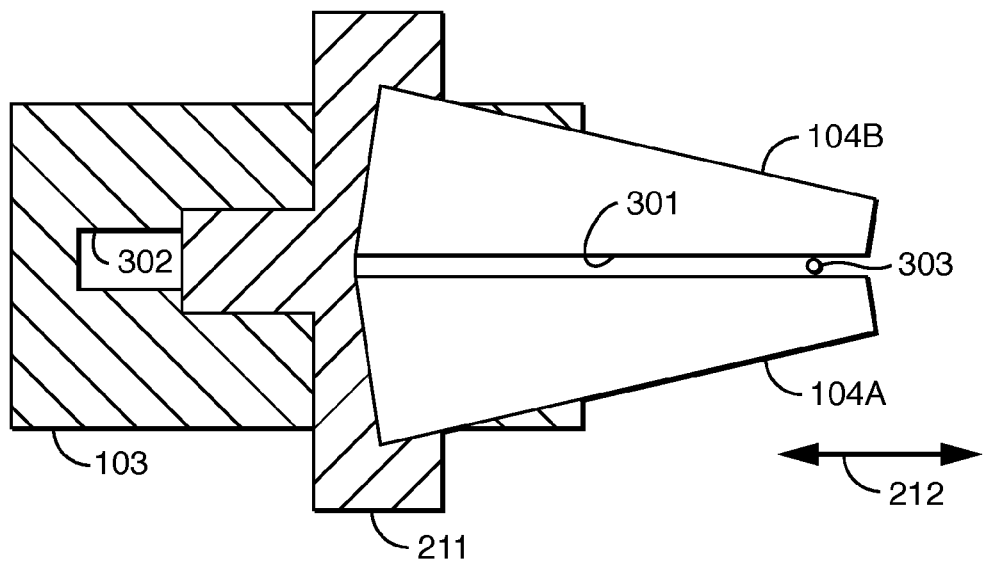
FIG. 3 is an exemplary schematic diagram depicting a top view of conical-forms mounted to a linearly-reciprocating motor, used in exemplary embodiments.

FIG. 3 is an exemplary schematic diagram depicting a top view 300 of conical-forms mounted to a linearly-reciprocating motor, used in exemplary embodiments. Conical members 104A and 104B essentially resemble truncated cones and are rigidly held by conical-form support 211 so that the geometrical axis of rotation of each truncated cone (the cones do not rotate) lies in the same plane which can be a horizontal plane. Other plane orientations can be used, and a particular orientation is described below in connection with FIG. 8. Conical members 104A and 104B and conical-form support 211 can all be constructed from metal and/or from rigid plastic or similar material.

Gap 301, to which reference was made above in discussion of FIG. 2, is slightly wider than a coated optical-fiber diameter. Gap 301 is shown between conical members 104A and 104B, and is depicted to have a constant gap distance between the two surfaces of those conical members, that distance being measured between imaginary lines on those surfaces containing their mutually-closest points. In other words, planes which are tangent to the surfaces of those cones at the locus of points on the surface of each cone that is closest to the surface of the other cone are parallel planes.

Transverse motor 103 includes a groove 302 running linearly in directions 212 into which conical-form support 211 is operatively connected. Thus, motor 103 can cause support 211 to have reciprocating motion in directions 212 by traveling within constraints of groove 302 (left to right and right to left in the FIG.) and support 211, in turn, causes both conical members 104A and 104B to have the same motion. Alternatively, as noted above, different fixed positions can be imposed and achieved by motor 103 instead of imposing a reciprocating motion.

Although not shown in FIG. 3, coated optical-fiber 108A is threaded between conical members 104A and 104B within gap 301, for example, at position 303 relative to the conical members at a given instant of time. Coated optical-fiber 108A in gap 301 is under constant tension from spring-loaded fiber holder 106B, need not move in either of directions 212 and, therefore, need not be overlayed on a cone when transverse motion in directions 212 of the cones is taking place. Otherwise the overlayed, coated optical-fiber could be dragged in directions 212 by the conical member over which it is wrapped. Therefore, synchronization can be added, at least to the extent that transverse movement in directions 212 is permitted to occur only when coated optical-fiber 108 is not wrapped over either cone, and occurs only when the coated optical-fiber 108 is in the vertical, neutral position. Thus, rotating arm 106A (FIG. 2) can be held motionless in place in a vertical, neutral position while movement of conical members in direction 212 occurs and after that movement stops, the rotating arm can start to rotate to its limit stop. When there is no conical-form transverse motion, a revolution from limit stop to limit stop can be continuous. Notably, when conical members 104A and 104B move to the right a larger bend radius (less bend stress) is imposed on the coated optical-fiber and when the conical members move to the left a smaller bend radius (more bend stress) is imposed on the coated optical-fiber.

Figure 4:
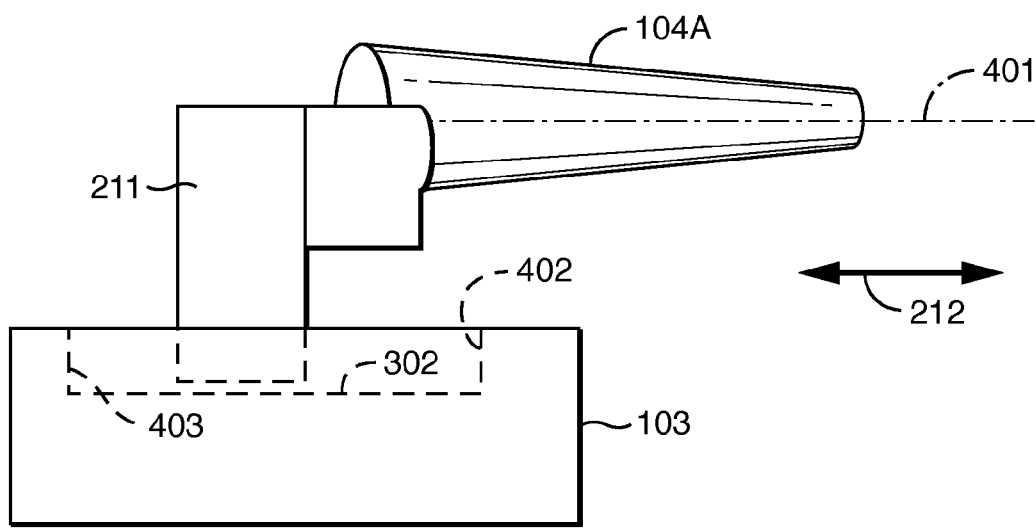
FIG. 4 is an exemplary schematic diagram depicting an elevation view of apparatus depicted in FIG. 3.

FIG. 4 is an exemplary schematic diagram depicting an elevation view 400 of apparatus depicted in FIG. 3. Conical member 104A is depicted as having a horizontal geometrical axis of rotation 401. Conical member 104B, having identical configuration to that of member 104A, is hidden from view in this FIG. Thus, conical member 104B also has a geometrical horizontal axis of rotation. (Both conical members do not rotate.) Transverse motor 103 causes motion of conical support 211 in directions 212 within groove 302, the motion to not exceed transverse limit stops 402/403. Coated optical-fiber 108 is not shown in this FIG.

Figure 5:
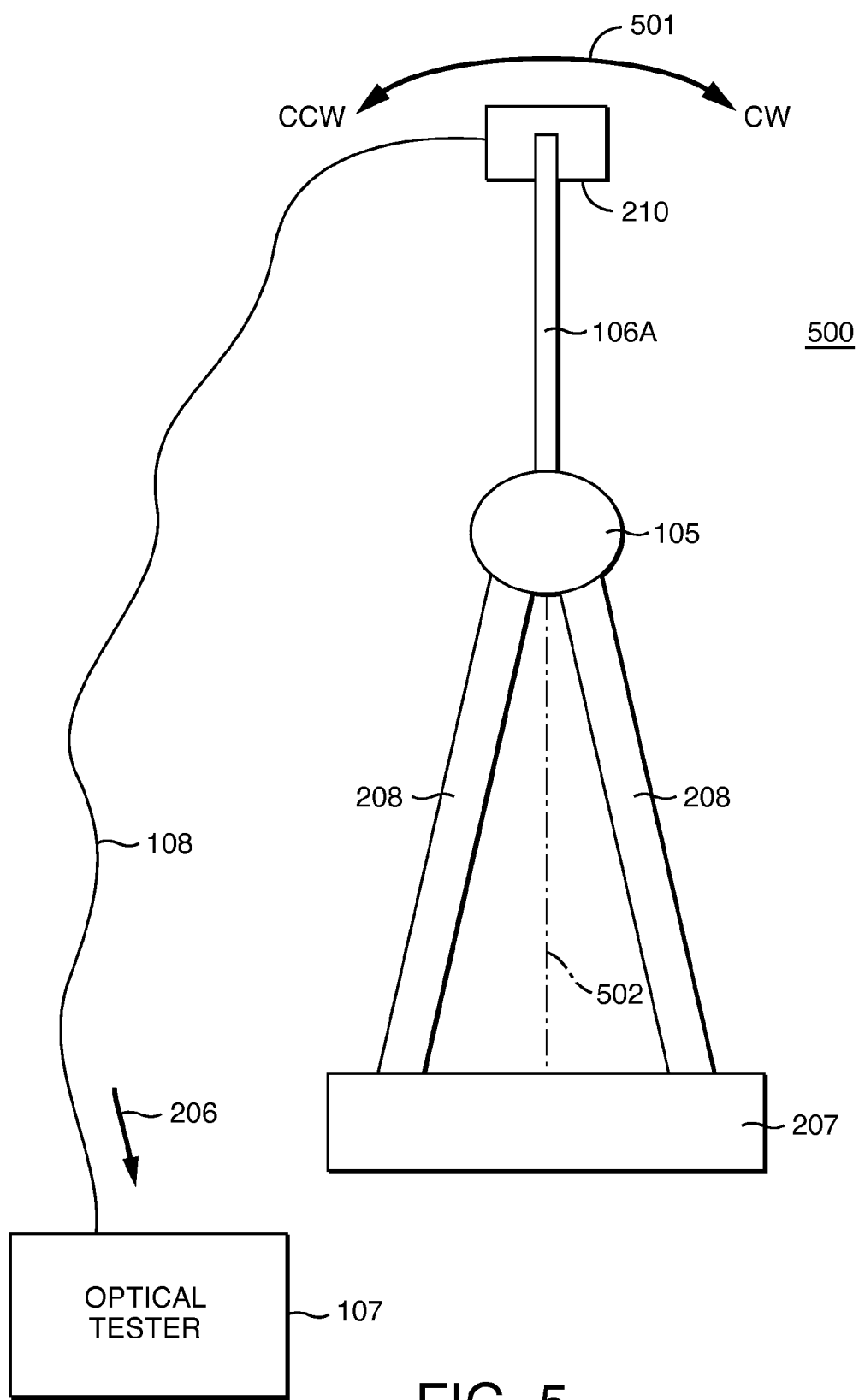
FIG. 5 is an exemplary schematic diagram depicting a side elevation view of a subset of the apparatus depicted in FIG. 2.

FIG. 5 is an exemplary schematic diagram depicting a side elevation view of a subset 500 of apparatus depicted in FIG. 2. In this view, base 207 is shown supporting two rigid legs 208 which, in turn, support rotational motor 105. Axel 209 is hidden from view, located on the opposite side of motor 105 from that which is shown. Rigid rotating arm 106A is connected from that axel to fiber holder 210 which moves in clockwise direction 501CW or in counter-clockwise direction 501CCW. Coated optical-fiber 108 is shown attached to fiber holder 210 at its highest point above ground in the rotation, and connected to optical tester 107.

When fiber holder 210 hits its limit stop in either CW or CCW directions, it stops at a vertical position designated by reference line 502, with holder 210 at the end of arm 106A then being located at its lowest position in the rotation, closest to ground. Thus, from the position of holder 210 that is shown in FIG. 5 with holder 210 at the end of arm 106A at its highest point to the position of holder 210 at its limit stop at the end of aim 106A at its lowest point (not shown), it has traveled in a first angular direction through a half circle from a top position (shown) to a bottom position (not shown). From that limit stop position, holder 210 travels in the opposite annular direction through a full circle until it hits the limit stop 502 again, but this time from the opposite direction. Possibly, holder 210 pauses at the highest point the neutral no-wrap point) in synchrony with transverse movement of conical member 104A/B, if that feature is included in the employed embodiment. This allows for a 180° wrap or overlay of coated optical-fiber around a first conical member and then allows for another 180° wrap or overlay around the other conical member. Since the conical members are identically dimensioned unless there is synchronized transverse movement of the cones between clockwise and counter-clockwise movements, the clockwise wrap and the counterclockwise wrap provide virtually identical bending radii. This range of motion provides substantial bending of the coated fiber for testing purposes and generates substantial data for analysis because the optical glass core and the inner and outer coatings are appropriately stressed over a full range of bending.

As noted, arm 106A can be held in the vertical position shown, with fiber holder 210 at top, until the conical members (not shown in this FIG.) are repositioned. As this movement is occurring, and as all movement is occurring, an optical signal can be continuously transmitted from optical tester 107 through coated optical-fiber 108, (transmission connection not shown in this FIG.) and are received by optical tester 107 via fiber 108 in direction 206.

Figure 6:
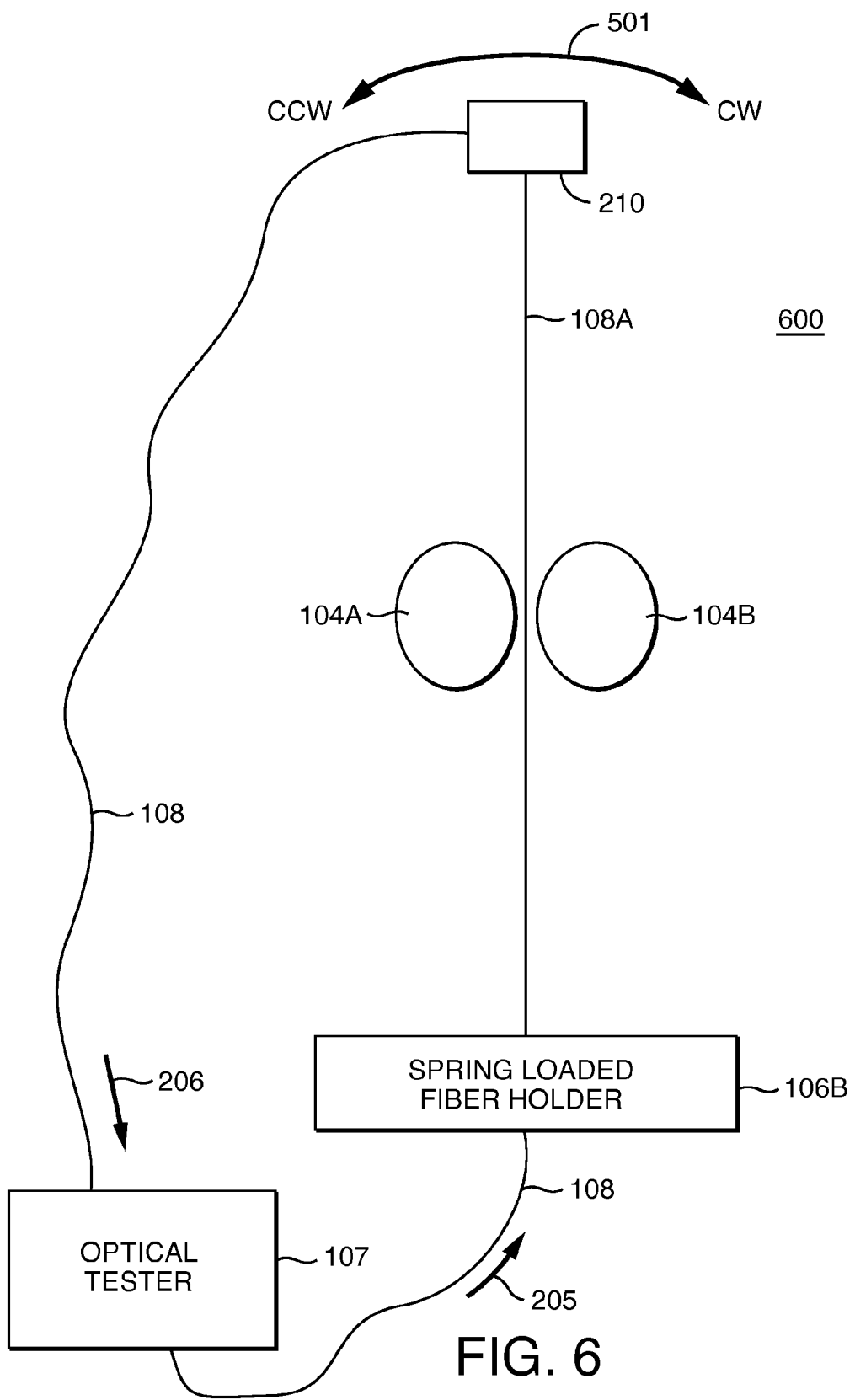
FIG. 6 is an exemplary schematic diagram depicting a side elevation view of another subset of the apparatus depicted in FIG. 2.

FIG. 6 is an exemplary schematic diagram depicting a side elevation view 600 of another subset of the apparatus depicted in FIG. 2. This view is taken in the same direction as that of FIG. 5. In FIG. 6, base 207, legs 208, motor 105 and arm 106A are not shown. However, conical forms 104A and 104B are shown, schematically, as ellipses because the path traced on the surface of those truncated cones by the overlayment of coated optical-fiber 108A are ellipses. Coated optical-fiber 108A is shown in the gap between the conical forms, held taut by spring loaded fiber holder 106B and fiber holder 210. Coated optical-fiber 108 including 108A makes a closed loop communicative connection with optical tester 107, as shown, with transmission and reception of signal occurring in directions 205 and 206, respectively. Direction of transmission is not critical and the optical signal can transmit in the opposite direction instead. As holder 210 rotates in angular directions 501CW or 501CCW, an overlayment of coated optical-fiber 108A upon conical forms 104B or 104A is readily visualized in FIG. 6.

FIG. 7 is an exemplary table from which a spreadsheet or multiple spreadsheets can be generated. FIG. 7 shows multiple variables that can be input and controlled in the testing of coated optical-fibers. Running from left to right across the top of the table are parameters that can be varied or held constant. For example, wavelength, signal power, bend radius, and fiber tension can all be held constant or one of these parameters can be varied, or all of these parameters can be varied, all under computer control and synchronization. In addition, various samples of coated optical-fiber, identified as Samples A, B and C, each having a different coating, can be tested against each other, under the same conditions.

Figure 8:
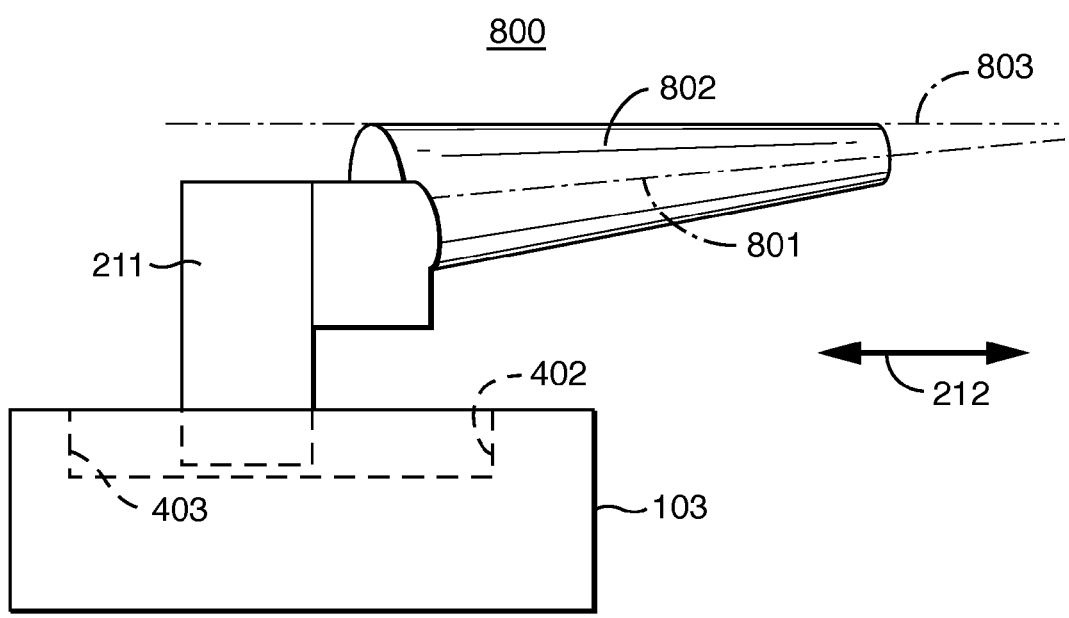
FIG. 8 is another exemplary schematic diagram depicting an elevation view of conical-form apparatus with particular angular orientation to mitigate any sliding of optical fiber.

FIG. 8 depicts another exemplary embodiment in a view similar to that of FIG. 4. However, in FIG. 8, geometrical axes of rotation of the two conical members (one conical member shown and the other not shown because it is hidden from view, and neither conical member rotates) are not in a horizontal plane. In other words, axis of rotation 801 of conical member 802 is not horizontal and is not depicted as horizontal. Rather, the top-most line of points lying on the surface of conical member 801 lies in a horizontal plane 803 which is shown on edge in FIG. 8. In other words, 803 appears as a horizontal line in FIG. 8. Also, the top-most line of points lying on the surface of the other conical member hidden from view also lies in the same horizontal plane. Movement of conical member 801 is in horizontal directions 212, as previously described between limit stops 402 and 403, as previously described.

The purpose of re-orienting the axes of rotation to achieve this configuration is to ensure that there is no slippage of the optical fiber (not shown in this FIG.) on the surface of the cone in the axial direction during a clockwise and counter-clockwise single revolution movement. In other words, because the top-most line of points on the surface of this configuration is horizontal, there is no possibility of that top-most line presenting a downward slope in the axial direction to the optical fiber as it is being wrapped clockwise or counterclockwise over the conical member. This embodiment is identical to the embodiment of FIG. 4 but for the slight change in angle of the axes of rotation of the conical members and, otherwise, operates identically to the operation of the embodiment of FIG. 4.

Regardless of ensuring no slippage by the embodiment of FIG. 8, the embodiment of FIG. 4 is operable with a variety of truncated cones and particularly with those having relatively gradual change in bend-radius as a function of displacement in the axial direction. In addition, any potential slippage on the surface of the cone of the embodiment of FIG. 4 during a single-revolution bend clockwise or counterclockwise can be further mitigated by making the conical surface ribbed and/or grooved to hold the fiber during a wrap. Further protection against slippage can be achieved by making the conical surface rubberized or the like, to increase surface friction forces. Moreover, because the optical fiber is held tautly by the optical fiber holders (optical fiber not shown in FIG. 4 or 8) as the fiber is wrapped clockwise and counterclockwise, there is no slack available to feed a slippage of the fiber transversely across the surface of the cone in its axial direction.

Figure 9:
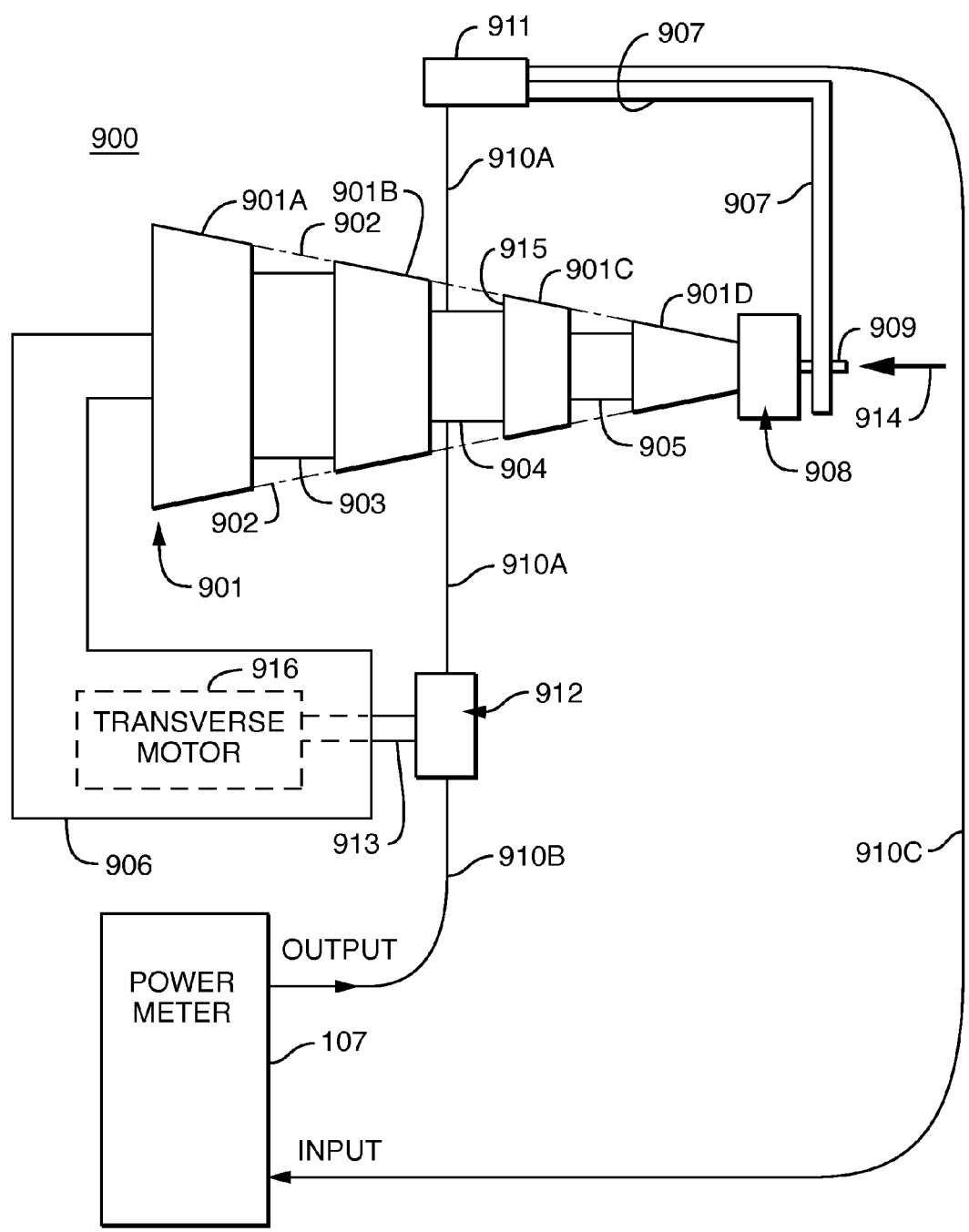
FIG. 9 is an exemplary schematic diagram of a single cone-cylinder embodiment permitting multiple test revolutions.

FIG. 9 depicts an exemplary embodiment 900 wherein a single conical-like and cylindrical-like member, i.e., a conical-cylindrical form 901, is used instead of two members. This embodiment permits a bending of the optical fiber comprised of a continuous wrapping of the optical fiber in the same clockwise (or counter-clockwise) direction for several revolutions, rather than being limited to no more than a single wrap in either clockwise or counter-clockwise direction. Truncated conical sections 901A, 901B, 901C and 901D together form the outline 902 of a truncated conical-like structure which can be referred to as conical-like structure 901 having conical outline(s) 902.

However, truncate conical-like structure 901 is further configured to include cylindrically-shaped portion 903 between sections 901 and 901B, cylindrically-shaped portion 904 between sections 901B and 901C, and cylindrically-shaped portion 905 between sections 901C and 901D, where the diameters of cylinders 903, 904 and 905 vary in relation to each other as shown in the FIG. Cylinder portion 903 presents the largest bend radius (least severe bend) and cylinder portion 905 presents the smallest bend radius (most severe bend) in FIG. 9. Multi-truncated, conical structure 901, including its cylindrical portions, can be fixedly supported by base 906. The geometrical axis of rotation of structure 901 can be horizontal (note that structure or member 901 does not rotate).

There can be more or fewer cylindrical sections configured in conical member 901 than those shown, and the cylindrical sections each offer a different bend radius. Further the cylinders' respective axial dimensions can be different from each other—they also can be long or short relative to the truncated conical surfaces 901A-D, or can be varied long and short in a regular or irregular pattern. Further, they can be sized differently from each other in an irregular manner; e.g., the bend radius of cylinder portion 904 need not necessarily be greater than the bend radius of cylinder portion 905. There is no restriction on the cylinders and truncated cones except that they must generally conform to the structure 901 with variations permitted as described above.

Rotational motor 908 and its axel 909 are similar in function and orientation to motor 105 and axel 209 of FIG. 2, but motor-axel combination 908/909 is itself mounted on the cone structure at the location where the apex of truncated conical member 901 would have been. Rotation arm 907 is affixed to axel 909 and rotates responsive to operation of motor 908 in a direction perpendicular to the plane of the drawing. Fiber holder system 911 is connected at the end of rotating arm 907 and, in combination with fiber clamp 912, holds fiber 910A tautly. Fiber clamp 912 is connected to piston 913 which, in turn, is connected to transverse motor 916 which can move fiber clamp 912 transversely, to the left or right, parallel to the geometrical axis of rotation of cone apparatus 901 (note that cone 901 does not rotate). The apparatus is designed to permit multiple bends, (in other words, an extended continuous bend) consisting of multiple clockwise revolutions, or multiple counterclockwise revolutions, of optical fiber 910A around each cylindrical surface of cylindrical portions 903, 904 and 905. The multiple revolutions are not made on any of the conically-related surfaces 901A, 901B, 901C or 901D. Optical fiber 910A is moved from one cylinder portion surface to the next as each cylinder surface's multiple windings is first completed and then unwound, the winding and unwinding being constrained by edges of that cylinder portion's abutting conical portions, as described below.

In this bending operation, characterized as a winding and unwinding operation, optical fiber 910A is bent in the sense that it is wound around cylinder sections, e.g., cylinder section 904, in a helix or spiral configuration. Thus, the wound optical fiber lies only directly on the surface of the cylinder at a substantially-constant bend angle and does not overlay itself—i.e., does not wind over a previously-wound section of the optical fiber. This is achieved by operation of fiber holder system 911 which makes the horizontal portion of rotatable arm 907 effectively a controlled-variable length. This is discussed in detail in connection with FIG. 10 below. Suffice it to say, for FIG. 9 discussion, that as arm 907 makes a revolution around the axis of rotation of axel 909, a mechanism located within fiber holder system 911 shortens the effective length of the horizontal portion of rotatable arm 907 sufficiently so that arm 907 clears, without entanglement, optical fiber 910A connected to optical fiber clamp 912. After several windings in the same direction, (in this example, looking in axial direction 914, windings are made counter-clockwise) before the constraint-end of cylinder portion 904 is reached, rotatable motor 908 stops and reverses direction to permit unwinding. When the optical fiber is completely unwound, which is the state shown in FIG. 9, movement to the next cylinder size can be made, or a repeat of the winding of the optical fiber at the same bend-radius cylinder 904 can be done, as desired.

Figure 10:
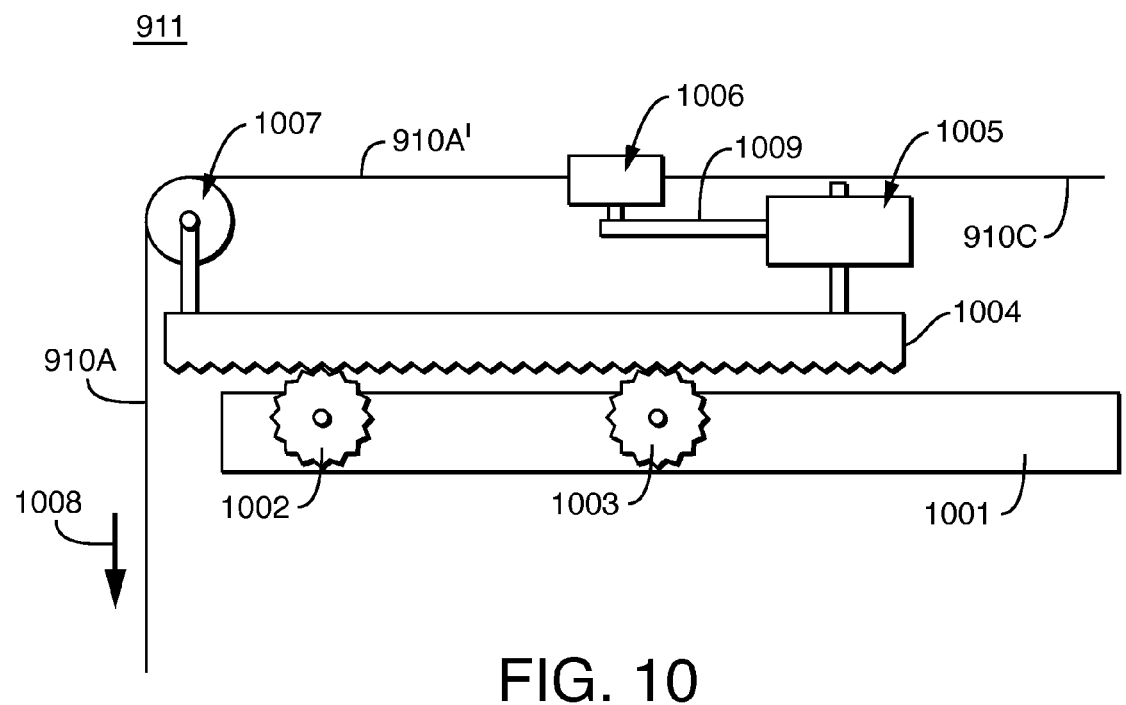
FIG. 10 is an exemplary schematic diagram of mechanisms that can be used in a fiber holder system attached to the end of the rotatable arm of FIG. 9, to provide functionality needed to implement the embodiment of FIG. 9.

Movement to a next cylinder bend-radius (higher or lower) is achieved by action of piston 913 in combination with action of mechanisms within fiber holder system 911, in further combination with controlled action of rotatable arm 907. FIG. 10 is an exemplary schematic diagram of mechanisms comprising fiber holder system 911 which is located at the end of rotatable arm 907 and, therefore, rotates with rotatable arm 907. Fiber holder system 911 includes a base 1001 affixed to and supported by the end of rotatable arm 907, motorized gears 1002 and 1003 supported by base 1001 engaging movable mount 1004 which moves left to right, a spring-torque mechanism 1005 fixedly mounted to movable mount 1004, fiber clamp 1006 connected to the spring-torque output portion of spring-torque mechanism 1005, and pulley 1007 affixed to movable mount 1004. Optical fiber 910A is draped over pulley 1007 and tautly connected to fiber clamp 1006.

In collision avoidance operation, when a helical overlay upon cylindrical section 904 (FIG. 9) is desired, as each revolution of rotation arm 907 is undertaken, gear teeth 1002 and 1003 are rotated clockwise by operation of rotational motors (not shown) affixed to base 1001 to cause transverse movement of movable mount 1004 to the right which, in turn, draws pulley 1007 to the right. Thus, fiber holder system 911, located at the end of arm 907, is drawn to the right sufficiently as it rotates so that it does not collide with fiber 910A connected to fiber clamp 912—fiber holder system 911 clears fiber 910A when making continuous revolutions. And, as each revolution progresses gear teeth 1002 and 1003 can be continuously rotated clockwise to ensure that the overlayed fiber is wound directly upon the cylindrical surface of cylinder section 904 in a helical pattern and not over a previously-wound portion of the fiber. The gear teeth rotation can be continuous as arm 907 rotates, or can be stepped under computer control in synchrony with rotational motion of arm 907 so that interference with fiber 910A is always avoided.

In the repositioning operation, when optical fiber 910A is to be re-positioned to a different cylindrical section, e.g., from its depicted position at cylinder 904 to a new, more severe-test cylinder section 905, both shown in FIG. 9, certain events must take place in sequence and in concert. First, rotation arm 907 can rotate from its depicted 12:00 o'clock (maximum height) position by about 90° in a clockwise direction when looking at the rotation in direction 914. This one-quarter turn moves optical fiber 910A away from the surface of cylinder 904 and away from cone structure 901 so that the optical fiber can clear lip 915 when it moves to cylindrical section 905. Next, transverse motor 916, under computer control, moves piston 913 to the right in synchrony with gear teeth 1002 and 1003 moving movable platform 1004 to the right. The displacement to the right is sufficient to align optical fiber 910A with cylinder 905 such that upon return of movable arm 907 to a 12 o'clock position optical fiber 910A would be tautly positioned and touching surface of cylinder section 905, ready for multiple counter-clockwise windings thereon.

One additional dynamic operation maintains tension in optical fiber 910A relatively constant as a function of number of windings around each cylinder and/or as a function of cylinder size. As each revolution is made, a portion of optical fiber equal in length to one circumference of its relevant cylinder is usurped and, if stress relief were not made for this operational fact, the optical fiber would ultimately break as it winds around the cylindrical form. FIG. 10 shows fiber clamp 1006 connected from spring torque mechanism 1005 which allows constant tension as member 1009 is expanded to the left, and returned to the right. As optical fiber 910A is drawn in direction 1008 because it is being wound-up, e.g., on a cylindrical structure 905, optical fiber clamp 1006 is drawn to the left and fiber portion 910A' between pulley 1007 and fiber clamp 1006 is foreshortened. The length of fiber portion 910A' is sufficient to permit the desired number of revolutions on cylindrical section 905, while expanding spring torque mechanism 1005 permits fiber clamp 1006 to maintain approximately constant tension on optical fiber 910A as it is being bent or wound around cylinder surface 905.

Thus, the embodiment of FIGS. 9 and 10 allows bend testing by way of multiple-revolutions of an optical fiber under the same variable conditions offered with the two-conical embodiment, such as different wavelengths, different power levels, different tensions in the fiber under test and different bend radii. Optical tester or power meter 107 in FIG. 9 provides unperturbed optical signal output to optical fiber section 910B and receives perturbed optical signal input from optical fiber section 910C, as optical fiber section 910A is stressed at various bend radii as described above. This signal flow occurs during the continuous bending, or winding, of the optical fiber over a cylindrical portion. Power meter 107 can be controlled to either provide, or not provide, an output signal during the time period associated with repositioning from a first cylinder to a second cylinder.

All necessary synchronization of signal flow and motor control is done via the computer arrangement shown in FIG. 1. Transverse motor 916 is synchronized by computer operation with rotational motor 908 and with motors (not shown) that rotate gears 1002 and 1003 so that repositioning of the optical fiber to a different cylinder radius can be achieved. Further, the gears are synchronized by computer operation with motor 908 to achieve clearance during each revolution and to achieve a helical overlay on the cylinder surface.

Optical-fiber coatings made from different chemical compositions will produce different operating results in terms of radiation leakage as a function of bend radius value and/or in terms of glass core fracture as a function of bend radius value. Some coatings may perform better for certain kinds of bend stresses, under certain ranges of fiber tension, certain ranges of optical signal power, or certain optical signal wavelengths. All of this data can be collected and organized to permit proper analysis. Computer 101 can be programmed to provide spreadsheet data holding all variables constant but for one, wherefore operating performance of each coating and glass being tested can be analyzed in terms of varying only one variable at a time. This valuable information shall aid in designing new and improved optical-fibers.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. For example, a dual cone embodiment could be constructed from two cones that have axes of rotation that are parallel to each other, wherefore the "gap" between the cones is not constant. The present invention is thus not to be interpreted as being limited to particular embodiments and the specification and drawings are to be regarded in an illustrative rather than restrictive sense.

What is claimed is:

1. Apparatus for bend fatigue testing a coated optical-fiber, said apparatus comprising:
a device for bending said optical-fiber only at one particular section of said optical-fiber, said section having a length substantially less than full length of said optical-fiber, and at a bend-radius limited to no less than a radius included within a controllable bend radius range of minimal values to provide said bend fatigue testing of said optical-fiber; and
an optical tester operatively connected to both ends of said optical-fiber for transmitting an optical signal via one of said ends and receiving said optical signal from the other of said ends during operation of said device, said transmitted optical signal and said received optical signal providing bend fatigue information about said optical-fiber.

2. Apparatus as recited in claim 1 wherein said device further comprises:
a mechanism for repeatedly bending and straightening said particular section of said optical-fiber, said repeatedly bending being limited to said bend-radius.

3. Apparatus as recited in claim 2 further comprising:
a computerized device for comparing said transmitted optical signal with said received optical signal over a period of time corresponding to duration of said operation of said repeatedly bending and straightening mechanism, to determine condition of said optical-fiber at any instant during said duration.

4. Apparatus as recited in claim 3 wherein said repeatedly bending mechanism further comprises:
a bi-directional mechanism for bending said optical-fiber in a clockwise direction and, after said straightening, bending said optical-fiber in a counterclockwise direction and, after said straightening, repeating operation of said bidirectional mechanism for duration of said operation of said repeatedly bending and straightening mechanism.

5. Apparatus as recited in claim 4 further comprising:
a computerized device for determining amount of deterioration of said received signal, compared with said transmitted signal, as a function of a number of cycles of said bending, and said straightening.

6. Apparatus as recited in claim 4 further comprising:
a mechanism for logging number of cycles of said bending and said straightening corresponding to fracture of said optical-fiber.

7. Apparatus as recited in claim 3 further comprising:
said computerized device introducing a number of variables into said testing selected from the group of variables consisting of optical signal power, optical signal wavelength, optical-fiber tension, optical-fiber bend-radius value and repetitively varying said optical-fiber bend-radius value; and
said computerized device providing a spreadsheet-like display of results of said optical-fiber testing as a function of any one or more of said variables.

8. Apparatus as recited in claim 2 wherein said repeatedly bending and straightening mechanism further comprises:
a bi-directional mechanism for bending, said optical-fiber in a clockwise direction and, after said straightening, bending said optical-fiber in a counterclockwise direction and, after said straightening, repeating operation of said bidirectional mechanism for duration of said operation of said repeatedly bending and straightening mechanism.

9. Apparatus as recited in claim 8 wherein said bi-directional mechanism further comprises:
two conical forms having axes of rotation lying in a plane, said two conical forms tapering in a common direction, and outside surfaces of said two conical forms being separated from each other by a gap having fixed gap distance, said gap distance being slightly larger than a diameter of said coated optical-fiber; and
a rotatable axel with axis of rotation being parallel to direction of said gap, an arm extending from, and fixedly connected to, said axel, and an optical-fiber holder affixed to the end of said arm holding said optical-fiber which is strung in said gap between said two conical forms.

10. Apparatus as recited in claim 9 wherein said plane is a horizontal plane.

11. Apparatus as recited in claim 10 wherein said axel is connected to a rotational motor supported by a fixed base, said rotational motor being limited in rotational motion to half circles in alternate clockwise and counter-clockwise directions.

12. Apparatus as recited in claim 11 wherein said conical forms are fixedly mounted to a transverse-movement, or reciprocating, motor which, when operating, moves both conical forms together in a horizontal direction parallel to said gap and said axel, whereby said bend-radius changes between limits established by said range of minimal values as a function of position of said conical forms.

13. Apparatus as recited in claim 2 wherein said optical tester further comprises:
a power controller for controlling power of said optical signal to be within minimum and maximum power values.

14. Apparatus as recited in claim 2 wherein said optical tester further comprises:
a wavelength selector for selecting wavelength of said optical signal to be within minimum and maximum wavelength values.

15. Apparatus as recited in claim 2 wherein said repeatedly bending and straightening mechanism further comprises:
a spring-loaded fiber holder for holding said optical-fiber in a manner to maintain constant, or near constant tension, forces within said optical-fiber during said operation of said repeatedly bending and straightening mechanism.

16. Apparatus of claim 1 wherein said device further comprises:
a conical-cylindrical structure configured to permit:
winding said optical-fiber over a first cylinder formed in said structure by operation of a rotatable arm holding said optical-fiber, said first cylinder having a first bend radius, said optical-fiber wound in a multiple-winding, first helical pattern;
un-winding said optical-fiber from said first cylinder by reverse operation of said rotatable arm;
moving said optical-fiber to a second cylinder framed in said structure by co-operation between said movable arm and a fiber holder, said second cylinder having a second bend radius;
re-winding said optical-fiber over said second cylinder by operation of said rotatable arm in a multiple-winding second helical pattern.

17. Apparatus of claim 16 wherein said optical tester comprises a power meter or an OTDR.

18. Apparatus of claim 16 further comprising:
a computer for synchronizing said winding, said un-winding, said moving and said re-winding with said optical signal transmitted by said optical tester, said computer also controlling said optical tester to transmit said optical signal at a particular power level and at a particular wavelength.

19. A method for bend fatigue testing a coated optical-fiber, said method comprising:
bending said optical fiber only at one particular section of said optical-fiber, said section having a length substantially less than full length of said optical-fiber, to provide said bend fatigue testing of said optical-fiber;
transmitting an optical signal from one end of said fiber and receiving said optical signal at the other end of said fiber while performing said bending to determine effects of bend fatigue upon said optical signal; and
obtaining information about a bend fatigue condition of said optical-fiber from a comparison of said received optical signal with said transmitted optical signal.

20. The method of claim 19 wherein said bending further comprises:
repetitively bending and straightening said optical-fiber.

21. The method of claim 20 wherein said obtaining information further comprises:
determining said condition of said optical-fiber as a function of multiple variables including said bending and said straightening.

22. The method of claim 21 wherein said multiple variables are selected from the group of variables consisting of power of said optical signal, wavelength of said optical signal, tension placed upon said optical-fiber during said bending and said straightening, and bend radius of said optical-fiber.

23. The method of claim 22 further comprising:
limiting said bend-radius to be no less than a radius value included within a bend-radius range of minimal radius values.

24. The method of claim 20 wherein said obtaining information includes using an optical tester operatively connected to both ends of said optical-fiber.

25. The method of claim 20 wherein said obtaining information comprises:
further determining said condition of said optical-fiber as a function of number of repetitions of said repetitive bending and straightening.

26. The method of claim 20 wherein said obtaining information comprises:
comparing said transmitted optical signal with said received optical signal over a period of time corresponding to duration of said operation of said repetitive bending and straightening mechanism, to determine condition of said optical-fiber at any instant during said duration.

27. The method of claim 20 wherein said repetitively bending and straightening further comprises:
first bending said optical-fiber in a clockwise direction and, after said straightening, next bending said optical-fiber in a counterclockwise direction and, after said straightening, repeating said first bending and said next bending for a predetermined time or a predetermined number of repetitions or until said optical-fiber fractures.

28. The method of claim 20 wherein said obtaining information further comprises:
using a computer device for
comparing said transmitted optical signal with said received optical signal during said repetitively bending and straightening to obtain condition of said optical-fiber at any instant during said repetitively bending and straightening, and
logging number of cycles of said repetitively bending and straightening corresponding to said any instant condition.

29. The method of claim 28 further comprising:
introducing a number of variables into said testing selected from the group of variables consisting of optical signal power, optical signal wavelength, optical-fiber tension, optical-fiber bend-radius value and repetitively varying said optical-fiber bend-radius value; and
providing a spreadsheet display of results of said optical-fiber testing as a function of any one or more of said variables.

30. The method of claim 20 further comprising:
repetitively varying bend-radius values of said optical-fiber during said repetitively bending and straightening said optical-fiber.

31. The method of claim 30 further comprising:
synchronizing frequency of said repetitively varying said bend-radius values with frequency of said repetitively bending and straightening said optical-fiber so that both frequencies are the same.

32. The method of claim 30 further comprising:
synchronizing frequency of said repetitively varying said bend-radius values with frequency of said repetitively bending and straightening said optical-fiber so that one frequency is an integer-multiple of the other frequency.

33. The method of claim 30 wherein said repetitively varying further comprises:
varying said bend radius values in a steadily increasing value direction, varying said bend radius values in a steadily decreasing value direction or varying said bend radius values in neither steadily increasing or steadily decreasing directions.

34. The method of claim 30 wherein said bend-radius values are held within predetermined minimum radius and predetermined maximum radius values.

35. The method of claim 19 wherein said bending further comprises:
winding, said optical-fiber over a conical-cylindrical structure in either a clockwise or counterclockwise direction so that said optical-fiber overlays a first cylindrical portion of said structure in a first helical pattern at a first pre-determined bend radius.

36. The method of claim 35 further comprising:
unwinding said first helical pattern;
re-positioning said optical-fiber to a second cylindrical portion of said structure having a second pre-determined bend radius; and
re-winding said optical-fiber over said second cylindrical portion of said structure in a second helical pattern at said second pre-determined bend radius.

37. The method of claim 35 or 36 further comprising:
controlling, by operation of a computer, said optical signal transmitting to not transmit during said re-positioning;
whereby said information about said condition of said optical-fiber is not obtained during said re-positioning.

38. The method of claim 36 wherein said transmitting further comprises:
applying an optical signal to said one end of said optical-fiber from a power meter, an optical tester or an OTDR.

39. The method of claim 38 further comprising:
synchronizing, by operation of said computer, said applying with said winding, said un-winding, said re-positioning and said re-winding.

40. The method of claim 39 further comprising:
controlling, by operation of said computer, said optical signal to be at a particular power level and at a particular wavelength.

41. The method of claim 40 wherein said controlling further comprises:
selecting said particular power level to change from a first power level when said optical-fiber forms said first helical pattern over said first cylindrical structure to a second power level when said optical-fiber forms said second helical pattern over said second cylindrical structure.

42. The method of claim 41 wherein said controlling further comprises:
selecting said particular wavelength to change from a first wavelength when said optical-fiber forms said first helical pattern over said first cylindrical structure to a second wavelength when said optical-fiber forms said second helical pattern over said second cylindrical structure.

* * * * *